United States Patent [19]
Sato et al.

[11] Patent Number: 5,545,737
[45] Date of Patent: Aug. 13, 1996

[54] PROCESS FOR SELECTIVELY PRODUCING AN (S)-9-FLUORO-3-METHYL-10-(4-METHYL-1-PIPERAZINYL)-7-OXO-2,3-DIHYDRO-7H-PYRIDO (1,2,3, -DE) (1,4) BENZOXAZINE-6-CARBOXYLIC ACID HEMIHYDRATE OR MONOHYDRATE

[75] Inventors: Yukio Sato; Atsushi Sato; Tatsuro Sumikawa; Tazuo Uemura, all of Tokyo, Japan

[73] Assignee: Daiichi Pharmaceutical Co., Ltd., Tokyo, Japan

[21] Appl. No.: 182,364

[22] Filed: Jan. 18, 1994

Related U.S. Application Data

[63] Continuation of Ser. No. 662,695, Mar. 1, 1991, abandoned.

[30] Foreign Application Priority Data

Mar. 1, 1990 [JP] Japan ................... 2-50454

[51] Int. Cl.$^6$ .................. C07D 498/06; C07D 498/16
[52] U.S. Cl. .................................................. 544/101
[58] Field of Search .................................. 544/101

[56] References Cited

U.S. PATENT DOCUMENTS

| | | | |
|---|---|---|---|
| 4,382,892 | 5/1983 | Hayakawa et al. | 544/101 |
| 4,607,046 | 8/1986 | Morita et al. | 514/399 |
| 4,628,111 | 12/1986 | Masmiba et al. | 560/159 |
| 5,053,407 | 10/1991 | Hayakawa et al. | 514/230.2 |
| 5,098,911 | 3/1992 | Ibrahim | 514/300 |

FOREIGN PATENT DOCUMENTS

| | | |
|---|---|---|
| 0206283 | 12/1986 | European Pat. Off. |
| 0354453 | 2/1990 | European Pat. Off. ...... 544/101 |
| 0203719 | 2/1983 | Germany . |
| 62-252790 | 11/1987 | Japan . |
| 90/04592 | 5/1990 | WIPO . |

OTHER PUBLICATIONS

"Techniques And Experiments for Organic Chemistry" by Ault pp. 55–58, 142–146. (1983).

*Primary Examiner*—Philip I. Daltow
*Attorney, Agent, or Firm*—Sughrue, Mion, Zinn, Macpeak & Seas

[57] ABSTRACT

A process for selectively producing an (S)-9-fluoro-3-methyl-10-(4-methyl-1-piperazinyl)-7-oxo-2,3 -dihydro-7H-pyrido[1,2,3-de][1,4]benzoxazine-6-carboxylic acid hemihydrate or monohydrate as depicted below, which comprises controlling the water content of an aqueous solvent in which an (S)-9-fluoro-3-methyl-10-(4-methyl-1-piperazin -yl)-7-oxo-2,3-dihydro-7H-pyrido[1,2,3-de][1,4]benzoxazine-6-carboxylic acid is dissolved during a crystallization.

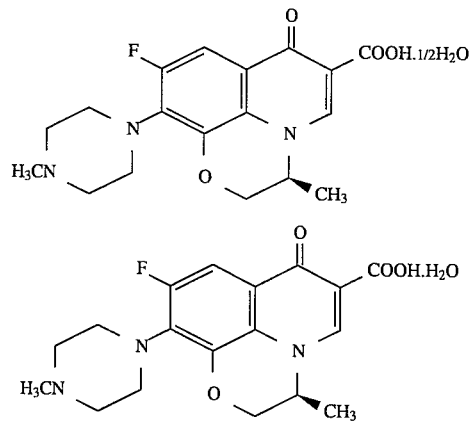

35 Claims, No Drawings

PROCESS FOR SELECTIVELY PRODUCING AN (S)-9-FLUORO-3-METHYL-10-(4-METHYL-1-PIPERAZINYL)-7-OXO-2,3-DIHYDRO-7H-PYRIDO (1,2,3, -DE) (1,4) BENZOXAZINE-6-CARBOXYLIC ACID HEMIHYDRATE OR MONOHYDRATE

This is a continuation of U.S. patent application Ser. No. 07/662,695 filed Mar. 1, 1991, now abandoned.

FIELD OF THE INVENTION

This invention relates to a process for the selective production of antimicrobial compounds ( S ) -9 -fluoro-3-methyl-10-(4-methyl-1-piperazinyl)-7-oxo-2,3 -dihydro-7H-pyrido[1,2,3-de][1,4]benzoxazine-6-carboxylic acid hemihydrate and monohydrate.

BACKGROUND OF THE INVENTION

Levofloxacine, which is a common name of (S)-9 -fluoro-3-methyl-10-(4-methyl-1-piperazinyl)-7-oxo-2,3 -dihydro-7H-pyrido[1,2,3-de][1,4]benzoxazine-6-carboxylic acid hemihydrate in accordance with JAN (Japanese Accepted Name), is a compound demonstrating high antimicrobial effect and high safety (refer to JP-A-62 -252790 or EP-A-0 206 283). The terms "JP-A" and "EP-A" as used herein mean an "unexamined published Japanese patent application" and "European patent publication", respectively. Thus, it is expected as an excellent synthetic antimicrobial agent.

In addition to levofloxacine which is a hemihydrate, crystals of (S)-9-fluoro-3-methyl-10-(4 -methyl-1-piperazinyl)-7-oxo-2,3-dihydro-7H-pyrido[1,2,3de][1,4]benzoxazine-6-carboxylic acid may be present in the form of a monohydrate differing in the number of water molecules in the crystal, or as anhydrous crystals obtained by dehydrating these hemi- and monohydrates.

A process is known for the production of levofloxacine which involves recrystallization or crystallization of levofloxacine from a solvent mixture of ethanol and diethyl ether or concentrated aqueous ammonia and ethanol (refer to JP-A-62-252790 or EP-A-0 206 283 as cited above). However, the use of the latter solvent mixture may cause the crystallization of (S)-9 -fluoro-3-methyl-10-(4-methyl-1-piperazinyl)-7-oxo-2,3 -dihydro-7H-pyrido[1,2,3-de][1,4] benzoxazine-6-carboxylic acid monohydrate, which will simply be called "monohydrate" hereinafter, together with the target levofloxacine (the hemihydrate form). The conversion of this monohydrate into the hemihydrate may be difficult to achieve in practice. Namely, when crystal water is removed from the monohydrate and the anhydrous crystals thus obtained are allowed to take up moisture, only the original monohydrate is obtained. When levofloxacine is contaminated with the monohydrate, therefore, the recrystallization or crystallization must be conducted till such contamination disappears.

Furthermore, anhydrous crystals obtained by removing crystal water cause blocking or sticking, and the industrial operations with them become troublesome. Accordingly, a method of preparing a hydrated crystal by the hydration of the dehydrated crystal is unsuitable as an industrial process.

SUMMARY OF THE INVENTION

Under these circumstances, the present inventors have conducted extensive studies. As a result, they have discovered that (S)-9-fluoro-3-methyl-10-(4-methyl -1-piperazinyl)-7-oxo-2,3-dihydro-7H-pyrido[1,2,3de][1,4]benzoxazine-6-carboxylic acid hemihydrate, i.e., levofloxacine, free from any monohydrate can be obtained by controlling the crystallization conditions. In addition, the inventors discovered that the solvent can be entirely removed without converting the product into the anhydrous crystals with undesirable characters such as sticking or blocking, and the target hemihydrate can be obtained by controlling the drying conditions. Thus, they have confirmed that the hemihydrate or monohydrate can be easily obtained without being contaminated with one another, thus completing the present invention.

The above and other objects and advantages are obtained by a process for selectively producing an (S) -9-fluoro-3-methyl-10-(4-methyl-1-piperazinyl)7-oxo2,3 -dihydro-7H-pyrido[1,2,3-de][1,4]benzoxazine-6-carboxylic acid hemihydrate or monohydrate, which comprises controlling the water content of an aqueous solvent in which an (S)-9-fluoro-3-methyl-10-(4-methyl-1-piperazinyl) -7-oxo-2,3-dihydro-7H-pyrido[1,2,3-de][1,4]benzoxazine-6 -carboxylic acid is dissolved during a crystallization.

DETAILED DESCRIPTION OF THE INVENTION

The present invention relates to a process for producing a hydrate of a synthetic antimicrobial agent. In one aspect, the present invention relates to a process for producing (S)-9-fluoro-3-methyl-10-(4 -methyl-1-piperazinyl)-7-oxo-2,3-dihydro-7H-pyrido[1,2,3de][1,4]benzoxazine-6-carboxylic acid hemihydrate, which comprises treating (S)-9-fluoro-3-methyl-10-(4-methyl-1 -piperazinyl)-7-oxo-2,3-dihydro-7H-pyrido[1,2,3-de][1,4] -benzoxazine-6-carboxylic acid in an aqueous solvent of relatively low water content.

It is preferable that the solvent has a water content which substantially prevents monohydrate crystal formation. One solvent which is preferably used is aqueous ethanol. More preferably, the solvent is aqueous ethanol with a water content ranging from about 2 to about 10%, more preferably from 4 to 5% (v/v). All water contents used herein are by volume per volume.

The solvent is preferably used in an amount of about 4 to about 8 times (e.g., about 400 ml to 800 ml/100 g; about 4 l to 8 l/1 kg; and so on), by volume, the amount, on a weight basis, of (S)-9-fluoro-3-methyl -10-(4-methyl-1-piperazinyl)-7-oxo-2,3-dihydro-7H-pyrido -[1,2,3-de][1,4]benzoxazine-6-carboxylic acid, more preferably 5 to 6 times the amount of (S)-9-fluoro-3 -methyl-10-(4-methyl-1-piperazinyl)-7-oxo-2,3-dihydro-7H-pyrido[1,2,3-de][1,4]benzoxazine-6-carboxylic acid.

A preferred embodiment of this aspect of the present invention comprises treating (S)-9-fluoro-3 -methyl-10-(4-methyl-1-piperazinyl)-7-oxo-2,3-dihydro-7H-pyrido[1,2,3-de][1,4]benzoxazine-6-carboxylic acid by dissolving in an aqueous solvent upon heating. Preferably, the heating temperature ranges from about 50° to about 80° C. More preferable, the heating temperature is about 80° C.

Another embodiment of this aspect of the present invention comprises treating (S)-9-fluoro-3-methyl-10 -(4-methyl-1-piperazinyl)-7-oxo-2,3- dihydro-7H-pyrido[1,2,3-de][1,4]benzoxazine-6-carboxylic acid by dissolving in an aqueous solvent upon heating followed by cooling. Preferably, the cooling temperature ranges from about −5° to about 25° C. More preferably, the cooling temperature is about 5° C. The cooling is preferably conducted for about 2 to about 20 hours, more preferably for about 4 hours.

A further aspect of the present invention comprises treating (S)-9-fluoro-3-methyl-10-(4-methyl-1 -piperazinyl)-7-oxo-2,3-dihydro-7H-pyrido[1,2,3-de][1,4] -benzoxazine-6-carboxylic acid in an aqueous solvent of relatively high water content or water to produce (S)-9 -fluoro-3-methyl-10-(4-methyl-1-piperazinyl)-7-oxo-2,3 -dihydro-7H-pyrido [1,2,3-de][1,4]benzoxazine-6-carboxylic acid monohydrate. Here, the solvent has a water content which substantially prevents hemihydrate formation. The aqueous solvent is preferably aqueous ethanol.

In addition to the hemihydrate (levofloxacine) and monohydrate crystal forms, (S)-9-fluoro-3-methyl-10 -(4-methyl-1-piperazinyl)-7-oxo-2,3-dihydro-7H-pyrido -[1,2,3-de][1,4]benzoxazine-6-carboxylic acid crystals may exist as anhydrous crystals. The present inventors examined the conversion of these crystals from one form to another, and thus successfully developed a method for converting hydrated and anhydrous crystals from one crystal form to another. The conversion method is summarized below.

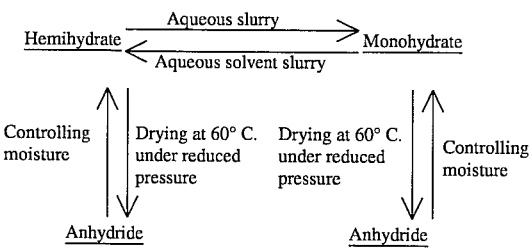

Among the conversion processes shown above, the conversion of the monohydrate into the hemihydrate will be described below.

In order to obtain the hemihydrate from the monohydrate, the monohydrate may be preferably treated by stirring a slurry of the monohydrate in an aqueous solvent with a specific water content of about 2 to about 10%. The conversion rate during this process is affected by the water content and treating temperature. Namely, the conversion rate for obtaining the hemihydrate at a constant temperature increases with decrease of the water content of the aqueous solvent. On the other hand, the conversion rate in an aqueous solvent with a constant water content increases with elevation of the treating temperature. For example, the conversion of the monohydrate into the hemihydrate in aqueous ethanol with a water content of 4% at 25° C. completes within about 30 minutes, while requiring about 5 hours at the same water content at 15° C. The conversion in aqueous ethanol with a water content of 8% at 40° C. completes within about 30 minutes, while the conversion hardly proceeds at 25° C. or below at the same water content.

A slurry can be prepared by mixing crystal with the solvent employed or by precipitating crystal from the solution of crystal.

As described above, the conversion of a hydrate is affected by the water content of the solvent employed, and the temperature and period of the treatment. As described above, a lower water content is preferable, e.g., 10% or less, more preferably 2 to 10%.

Any water miscible solvent may be used in the conversion of the monohydrate into the hemihydrate if the monohydrate is soluble therein. Examples include lower alcohols such as methanol, ethanol and propanol, and acetone. Among these solvents, ethanol is most preferable.

On the other hand, the conversion of the hemihydrate into the monohydrate may be conducted by stirring a slurry of the hemihydrate in water or an aqueous solvent with a specific water content. Similar to the conversion from monohydrate into hemihydrate, the conversion rate from hemihydrate into monohydrate in this instance is affected by various factors including temperature. The conversion in water proceeds more rapidly at a higher temperature. For example, the conversion is completed within about 4 hours at 40° C. but requires about 42 hours at 5° C.

Contrary to the conversion from the monohydrate to the hemihydrate, a high water content is preferable, e.g., 10% or more.

The stabilities of the hemihydrate and monohydrate in a slurry in an aqueous solvent were examined. As a result, it has been revealed that the stabilities of the hydrates in a slurry in an aqueous solvent depend on the water content of the aqueous solvent employed, the treating temperature and the treating period.

When the stirring is conducted at a high temperature within a short period of time, the stable form of crystal is the hemihydrate even at a high water content. When the stirring temperature is low, on the other hand, the hemihydrate is present as the stable form at a relatively lower water content even for a long period of time.

For example, when the stirring is conducted at 50° C. for 60 hours, the hemihydrate is present as the stable form at a water content of 16%. When the water content is elevated to 20%, the monohydrate is present as the stable form. When the stirring is conducted at 40° C., the water content, at which the hemihydrate can be present as the stable form, is as low as 10%. It is possible in this case, however, to prolong the stirring period to 8 hours or longer. At this temperature, the monohydrate is present as the stable form at a water content of 14%, however, both the hemihydrate and monohydrate are observed at a water content of 12%. When the stirring is conducted at 20° C. for 24 hours, the hemihydrate is present as the stable form at a water content of 8%, while the monohydrate is present as the stable form at a water content of 12%. Both hydrates are observed together at a water content of 10%. When the stirring is conducted at 5° C. for 3 days, the hemihydrate is present as the stable form at a water content of 6% while the monohydrate is present as the stable form at a water content of 8%.

These results clearly show that the target hemihydrate free from any monohydrate can be obtained by using a solvent of a low water content in the recrystallization or crystallization of levofloxacine, and preferably dissolving the crystals by heating within a short period of time and then immediately conducting the crystallization at a low temperature. On the other hand, the above-mentioned examination on the stabilities of the hydrates in a slurry shows that a process for producing the hemihydrate may be changed into a process for producing the monohydrate by, for example, elevating the temperature or prolonging the period of the treatment.

Based on these findings, particular conditions for the recrystallization or crystallization are discussed. Namely, crude levofloxacine crystals are dissolved in an aqueous solvent by heating and then immediately cooled so as to induce crystallization.

The heating temperature at the dissolution may preferably range from about 50° to about 80° C., more preferably about 80° C. The cooling temperature may range from about −5° to about 25° C., preferably about 5° C. The cooling period may range from about 2 to about 20 hours, preferably about 4 hours.

When the water content of the solvent is, for example, as high as 50% at the dissolution of the crystals, it is sufficient to use about three times as much solvent based on the crystals (volume/weight). In this case, however, the obtained hemihydrate crystals can be contaminated with the monohydrate, which suggests that this ratio of solvent to crystals is unsuitable for producing levofloxacine at such high water content. On the other hand, the amount of the solvent required in the crystallization increases with decrease of the water content (e.g., from 50% to about 5%) of the solvent, for example, 5 to 6 times as much as the crystals. In this case, however, the desired hemihydrate can be exclusively obtained and a high yield of 95% is achieved.

The amount of the solvent may range from about 4 to about 8 times, preferably from 5 to 6 times, based on the amount of the crystals (volume/weight). It is not always required to use the solvent in the amount as specified above from the beginning of the treatment. Namely, the levofloxacine may be preliminarily dissolved in a larger amount of the solvent and then the resulting solution may be concentrated so as to control the amount of the solvent.

Also, the particle size of the crystals obtained by the crystallization can be controlled by adjusting the water content of the solvent. In the case of aqueous ethanol, the particle size increases with increase of the water content. The maximum particle size (about 18 μm) is achieved at a water content of about 11%. When the water content further increases, however, the particle size does not increase further but rather decreases.

Most preferably, the crystallization of levofloxacine is conducted with the use of ethanol with a water content of about 5%, in order to obtain levofloxacine crystals with a small particle size.

Furthermore, it is also possible to employ some purification steps (for example, decoloration with the use of active carbon) between the dissolution of the crude crystals and the recrystallization or crystallization.

Also, in the process of the selective production of an (S)-9-fluoro-3-methyl-10-(4-methyl-1-piperazinyl) -7-oxo-2,3-dihydro-7H-pyrido[1,2,3-de][1,4]benzoxazine-6-carboxylic acid hemihydrate or monohydrate in accordance with the present invention, the water content may be controlled by adding water after mixing an (S)-9-fluoro -3-methyl-10-(4-methyl-1-piperazinyl)-7-oxo-2,3-dihydro -7-pyrido[1,2,3-de][1,4]benzoxazine-6-carboxylic acid with a solvent.

A method for drying the crystals is described below.

The result of differential thermal analysis indicates that crystal water is liberated from crystals of levofloxacine at about 70° C. under atmospheric pressure or at about 60° C. under reduced pressure to result in anhydrous crystals. The process which comprises completely removing the solvent and the crystal water and then producing the hemihydrate by controlling the moisture is unsuitable, since the anhydride shows a poor property. In order to remove the solvent alone from the aimed product, therefore, the temperature, degree of the reduction of pressure and time of drying must be controlled.

Therefore, the drying temperature preferably ranges from about 20° to about 45° C., more preferably from 35° to 40° C. The reduced pressure preferably ranges from about 5 to about 100 mmHg, more preferably from 5 to 10 mmHg. The drying time is preferably 8 hours or less.

The drying method is applicable to various dryers, for example, conical-screw drier, vibro-fluidizing drier, double-cone rotating drier or compartment tray drier.

To further illustrate the present invention, and not by way of limitation, the following Examples are given.

EXAMPLE 1

28.9 kg of crude crystals of levofloxacine [(S) -9-fluoro-3-methyl-10-(4-methyl-1-piperazinyl)-7-oxo2,3 -dihydro-7H-pyrido[1,2,3-de][1,4]benzoxazine-6-carboxylic acid hemihydrate] were dissolved in 375 l of 4% aqueous ethanol under stirring. After adding 0.87 kg of active carbon, the obtained mixture was filtered. The active carbon was washed with 4% aqueous ethanol. The filtrate and the washing liquid were combined and concentrated so as to give a total volume of about 5 times (volume/ weight) the initial levofloxacine crystals. After the completion of the concentration, the mixture was allowed to cool under stirring overnight. Then, it was allowed to stand while cooling to 7° to 15° C. for 3 to 4 hours to thereby induce crystallization. The crystals thus precipitated were collected by filtering. Thus 26.7 kg of the crystals were obtained. These crystals were packed into a conical-screw drier and dried therein under reduced pressure at an elevated temperature for 4 hours. Thus 25.8 kg of dry levofloxacine was obtained. This product was identified as levofloxacine by instrumental analyses. The physical data of the levofloxacine (hemihydrate) are as follows:

Melting point: 223°–225° C. (decomp.)

Elemental analysis: as $C_{18}H_{20}FN_3O_4 \cdot \frac{1}{2}H_2O$ Calculated: C 58.37, H 5.71, N 11.35 Found: C 58.32, H 5.43, N 11.37

Water content (Karl-Fischer's method): Calculated: 2.43% Found: 2.50%

Differential thermal analysis: Crystal water liberation point: 72.4° C. Weight change: 2.5% (calculated: 2.43%) Melting point: 234.0° C.

Powder method of X-ray diffraction (characteristic Peak):

$$2\theta = 6.7°$$
$$13.2°$$

IR (characteristic peak): 3440 cm$^{-1}$

In the above-mentioned analyses, the following instruments were employed.

Water content: MKA-210, Kyoto Denshi Kogyo K.K.

Melting Point: 535, Büch Co. (determined in accordance with The Pharmacopoea of Japan)

Differential thermal analysis: TG/DTA20, Seiko I & E. Controller, SSC/580

Powder method of X-ray diffraction: Geigerflex, Rigaku Denki K.K.

IR: 260-30, Hitachi Electric Co.

EXAMPLE 2

5.05 kg of crude levofloxacine crystals and 5% aqueous ethanol were treated in the same manner as described in Example 1 resulting in 5.0 kg of crystals. These crystals were packed into a vibro-fluidizing drier and dried under reduced pressure for about 3.5 hours. Thus 4.67 kg of dry levofloxacine was obtained.

EXAMPLE 3

13.2 kg of crude levofloxacine crystals and 5% aqueous ethanol were treated in the same manner as the one described in Example 1 resulting in 5.0 kg of crystals. These crystals were packed into a double-cone rotating drier and dried for about 3.5 hours. Thus 12.1 kg of dry levofloxacine was obtained.

EXAMPLE 4

5 g of crude levofloxacine crystals were added to 25 ml of water and formulated into a slurry. The obtained slurry was stirred at 25° C. for 20 hours. The crystals were collected by filtering, washed with 5 ml of water and dried at room temperature under reduced pressure. When a constant weight was achieved, 4.76 g of (S)-9-fluoro-3-methyl-10-(4-methyl-1-piperazinyl)-7 -oxo-2,3-dihydro-7H-pyrido[1,2,3-de][1,4]-benzoxazine-6-carboxylic acid monohydrate was obtained. The analysis on these crystals by the powdery method of X-ray diffraction proved that the product was the monohydrate.

The physical date of the monohydrate are as follows:

Melting point: 225°–228° C. (decomp.)

Elemental analysis: as $C_{18}H_{20}FNØ_3O_4 \cdot H_2O$ Calculated: C 56.93, H 5.80, N 11.07 Found: C 57.05, H 6.11, N 11.05

Water content (Karl-Fischer's method): Calculated: 4.74% Found: 4.70%

Differential thermal analysis: Crystal water liberation point: 62.0° C. Weight change: 4.8% (calculated: 4.74%) Melting point: 232.7° C.

Powder method of X-ray diffraction (characteristic peak):

$$2\theta = \quad 8.0°$$
$$11.5°$$
$$16.7°$$
$$18.0°$$
$$22.5°$$

IR (characteristic peak): 3540, 3440 $cm^{-1}$

In the above-mentioned analyses, the same instruments as described in Example 1 were employed.

EXAMPLE 5

5 g of crude levofloxacine crystals were added to 50 ml of water and then treated in the same manner as described in Example 4. Thus 4.44 g of (S)-9-fluoro-3 -methyl-10-(4-methyl-1-piperazinyl)-7-oxo-2,3-dihydro-7H-pyrido[1,2,3-de][1,4]-benzoxazine-6-carboxylic acid monohydrate was obtained.

The process of the present invention enables the selective production of levofloxacine, i.e., crystalline hemihydrate, from (S)-9-fluoro-3-methyl-10-(4-methyl-1 -piperazinyl)-7-oxo-2,3-dihydro-7H-pyrido[1,2,3-de][1,4] -benzoxazine-6-carboxylic acid, which occurs in several crystalline forms, on an industrial scale. In addition, it enables the production of the monohydrate. Furthermore, it enables the adjustment of the particle size of the target compound by controlling the crystallization conditions. Thus, crystals of an appropriate particle size can easily be obtained. In addition, the drying method in accordance with the present invention is applicable to various drying systems.

Therefore the process of the present invention is highly useful from industrial and economical viewpoints.

While the invention has been described in detail and with reference to specific embodiments thereof, it will be apparent to one skilled in the art that various changes and modifications can be made therein without departing from the spirit and scope thereof.

What is claimed is:

1. A process for selectively producing an (S)-9-fluoro-3 -methyl-10-(4-methyl-1-piperazinyl)-7-oxo-2,3-dihydro-7H -pyrido[1,2,3-de][1,4]benzoxazine-6-carboxylic acid hemihydrate, comprising the step of controlling the water content of an aqueous solvent selected from the group consisting of methanol, ethanol, propanol and acetone having (S)-9-fluoro-3-methyl-10-(4-methyl -1-piperazinyl)-7-oxo-2,3-dihydro-7H-pyrido[1,2,3de][1,4]benzoxazine-6 -carboxylic acid dissolved therein during a crystallization reaction, wherein said water content of said solvent ranges from about 2 to about 10%.

2. The process as claimed in claim 1, wherein said aqueous solvent is ethanol.

3. The process as claimed in claim 1, wherein the water content of said solvent ranges from 4 to 5%.

4. The process as claimed in claim 1, wherein said solvent is used in an amount of about 4 to about 8 times, by volume, the amount, on a weight basis, of said (S)-9-fluoro-3-methyl-10-(4-methyl-1-piperazinyl)-7-oxo -2,3-dihydro-7H-pyrido[1,2,3-de][1,4]benzoxazine-6-carboxylic acid crystal form dissolved therein.

5. The process as claimed in claim 4, wherein said solvent is used in an amount of from 5 to 6 times, by volume, the amount, on a weight basis, of said (S)-9 -fluoro-3-methyl-10-(4-methyl-1-piperazinyl)-7-oxo-2,3 -dihydro-7H-pyrido[1,2,3-de][1,4]benzoxazine-6-carboxylic acid crystal form dissolved therein.

6. The process as claimed in claim 1, further comprising dissolving said (S)-9-fluoro-3-methyl-10-(4 -methyl-1-piperazinyl)-7-oxo-2,3-dihydro-7H-pyrido[1,2,3de][1,4]benzoxazine-6-carboxylic acid crystal form in said aqueous solvent under heating conditions.

7. The process as claimed in claim 6, wherein the heating temperature ranges from about 50° to about 80° C.

8. The process as claimed in claim 7, wherein the heating temperature is about 80° C.

9. The process as claimed in claim 6, further comprising cooling the reaction mixture after said dissolution step under heating conditions.

10. The process as claimed in claim 9, wherein the cooling temperature ranges from about −5° to about 25° C.

11. The process as claimed in claim 10, wherein the cooling temperature is about 5° C.

12. The process as claimed in claim 9, wherein said cooling is conducted for about 2 to about 20 hours.

13. The process as claimed in claim 9, wherein said cooling is conducted for about 4 hours.

14. The process as claimed in claim 1, further comprising removing said solvent alone from the hemihydrate crystals formed during crystallization by controlling drying conditions to prevent formation of anhydrous crystals.

15. The process as claimed in claim 14, wherein said controlling drying conditions comprises controlling temperature, degree of reduction of pressure and time of drying.

16. The process as claimed in claim 15, wherein the drying temperature ranges from about 20° to about 45° C., the reduced pressure ranges from about 5 to about 100 mmHg, and the drying time is up to about 8 hours.

17. The process as claimed in claim 1, wherein the crystal form dissolved in said aqueous solvent is crude levofloxacine.

18. A process as claimed in claim 5, wherein the water content of the aqueous ethanol ranges from 4 to 5%.

19. A process for selectively producing an (S)-9-fluoro-3 -methyl-10-(4-methyl-1-piperazinyl)-7-oxo-2,3-dihydro -7H-pyrido[1,2,3-de][1,4]benzoxazine-6-carboxylic acid monohydrate, comprising the step of controlling the water content of an aqueous solvent having an (S)-9-fluoro-3-methyl-10-(4-methyl-1 -piperazinyl)-7-oxo-2,3-dihydro-7H-pyrido[1,2,3-de][1,4]benzoxazine -6-carboxylic acid dissolved therein during a crystallization reaction, wherein said water content is at least 10%.

20. The process as claimed in claim 19, wherein the aqueous solvent is water.

21. The process as claimed in claim 19, wherein said aqueous solvent is aqueous ethanol.

22. The process as claimed in claim 19, wherein said solvent is used in an amount of about 4 to about 8 times, by volume, the amount, on a weight basis, of said (S)-9-fluoro-3-methyl-10-(4-methyl-1-piperazinyl)-7-oxo-2,3-dihydro-7H-pyrido [1,2,3de] [1,4]benzoxazine-6-carboxylic acid crystal form dissolved therein.

23. The process as claimed in claim 22, wherein said solvent is used in an amount of from 5 to 6 times, by volume, the amount, on a weight basis, of said (S)-9-fluoro-3-methyl-10-(4-methyl-1-piperazinyl)-7-oxo-2,3-dihydro-7H-pyrido[1,2,3-de][1,4]benzoxazine-6-carboxylic acid crystal form dissolved therein.

24. The process as claimed in claim 19, further comprising dissolving said (S)-9-fluoro-3-methyl-10-(4-methyl-1-piperazinyl)-7-oxo-2,3-dihydro-7H-pyrido[1,2,3-de][1,4]benzoxazine-6-carboxylic acid crystal form in said aqueous solvent under heating conditions.

25. The process as claimed in claim 24, wherein the heating temperature ranges from about 50° to about 80° C.

26. The process as claimed in claim 25, wherein the heating temperature is about 80° C.

27. The process as claimed in claim 24, further comprising cooling the reaction mixture after said dissolution step under heating conditions.

28. The process as claimed in claim 27, wherein the cooling temperature ranges from about −5° to about 25° C.

29. The process as claimed in claim 28, wherein the cooling temperature is about 5° C.

30. The process as claimed in claim 27, wherein said cooling is conducted for about 2 to about 20 hours.

31. The process as claimed in claim 30, wherein said cooling is conducted for about 4 hours.

32. The process as claimed in claim 19, further comprising removing said solvent alone from the monohydrate crystals formed during crystallization by controlling drying conditions to prevent formation of anhydrous crystals.

33. The process as claimed in claim 32, wherein said controlling drying conditions comprises controlling temperature, degree of reduction of pressure and time of drying.

34. The process as claimed in claim 33, wherein the drying temperature ranges from about 20° to about 45° C., the reduced pressure ranges from about 5 to about 100 mmHg, and the drying time is up to about 8 hours.

35. The process as claimed in claim 19, wherein the crystal form dissolved in said aqueous solvent is crude levofloxacine.

* * * * *